United States Patent [19]

Singh et al.

[11] Patent Number: 5,898,005

[45] Date of Patent: *Apr. 27, 1999

[54] RAPID DETECTION OF ANALYTES WITH RECEPTORS IMMOBILIZED ON SOLUBLE SUBMICRON PARTICLES

[75] Inventors: Pratap Singh, Miami; Fred Moll, III, Pembroke Pines; Peter Cronin, Miami; Spencer H. Lin, Coral Springs, all of Fla.; Charles Ferzli, Carrboro, N.C.; Kent Koski, Hialeah, Fla.; Richard Saul, Gaithersburg, Md.

[73] Assignee: Dade Behring Inc., Deerfield, Ill.

[ * ] Notice: This patent is subject to a terminal disclaimer.

[21] Appl. No.: 08/227,364

[22] Filed: Apr. 13, 1994

Related U.S. Application Data

[63] Continuation-in-part of application No. 08/021,928, Feb. 24, 1993, abandoned, and a continuation-in-part of application No. 08/226,172, Apr. 12, 1994.

[51] Int. Cl.[6] .................................................. G01N 33/552
[52] U.S. Cl. ........................ 436/527; 435/7.93; 435/7.94; 436/500; 436/512; 436/530; 436/823; 530/391.1
[58] Field of Search ..................... 436/500, 512, 436/527, 530, 823; 435/7.93, 7.94; 530/391.1

[56] References Cited

U.S. PATENT DOCUMENTS

| | | |
|---|---|---|
| 4,363,634 | 12/1982 | Schall, Jr. . |
| 4,507,466 | 3/1985 | Tomalia et al. ........................ 528/332 |
| 4,517,288 | 5/1985 | Giegel et al. ........................... 435/188 |
| 4,568,737 | 2/1986 | Tomalia et al. ........................ 528/332 |
| 4,694,064 | 9/1987 | Tomalia et al. ........................ 528/332 |
| 5,204,448 | 4/1993 | Subramanian .......................... 530/408 |
| 5,468,606 | 11/1995 | Bogart et al. ............................... 435/6 |
| 5,482,830 | 1/1996 | Bogart et al. ........................... 436/525 |

FOREIGN PATENT DOCUMENTS

| | | |
|---|---|---|
| 0481526 | 4/1992 | European Pat. Off. . |
| 8801178 | 2/1988 | WIPO . |
| 9012050 | 10/1990 | WIPO . |
| WO 91/12886 | 9/1991 | WIPO . |
| 9306868 | 4/1993 | WIPO . |
| WO 94/03774 | 2/1994 | WIPO . |

OTHER PUBLICATIONS

American Chemical Society Symposium Series vol. 70, Proceedings of the American Chemical Society Division of Polymeric Materials: Science and Engineering, Singh, et al., San Diego, California pp. 237–238 (1994).

Giegel et al., Clin.Chem. 28: 1894–98 (1982).

Roberts, J.C. et al., Using Starburst Dendrimers as Linker Molecules to Radiolabel Antibodies, Bioconjug. Chemistry 1: 305–308 (1990).

*Primary Examiner*—Mary E. Ceperley
*Attorney, Agent, or Firm*—Ronald C. Lundquist

[57] ABSTRACT

Methods are provided for conducting specific binding assays to determine the concentration or presence of at least one analyte in a sample. Dendrimer-reagent preparations with particular analyte specificities are mixed in solution with a sample to form dendrimer-reagent-sample complexes. The complexes are then immobilized on a solid phase. Immobilization is facilitated by coupling specific binding assay reagents such as polypeptide receptors or analytes with water soluble polymers. Such water soluble polymers, for example star polymers such as dendrimers, provide production advantages of lot-to-lot uniformity and homogeneity, and can enhance sensitivity due to low non-specific binding to the solid phase.

32 Claims, 10 Drawing Sheets

RAPID DETECTION OF ANALYTES WITH RECEPTORS IMMOBILIZED ON SOLUBLE SUBMICRON PARTICLES

This is a continuation-in-part of application Ser. No. 08/021,928, filed Feb. 24, 1993, now abandoned, and is a continuation-in-part of application Ser. No. 08/226,172, filed Apr. 12, 1994.

FIELD OF THE INVENTION

This invention relates generally to methods for immobilizing specific binding assay reagents on a solid support. In particular this invention relates to methods of mixing reagents with samples in solution to form reagent-sample complexes and immobilizing the reagent-sample complexes on a solid phase support using water soluble polymers.

BACKGROUND OF THE INVENTION

In vitro diagnostic assays may be used to measure amounts of an analyte found in a body fluid sample or tissue sample. The analyte must be distinguished from other components found in the sample. Analytes may be distinguished from other sample components by reacting the analyte with a specific receptor for that analyte. Assays that utilize specific receptors to distinguish and quantify analytes are often called specific binding assays.

The most common receptors are antibodies and specific binding proteins such as Intrinsic Factor or Folate Binding Protein. Receptors are characterized by having a reversible specific binding affinity for an analyte or an analogue of that analyte. As used herein, an analogue generally is an analyte derivative carrying a detectable marker such as an enzyme, fluorescent molecule or other known label. The analogue is capable of binding to a receptor with about the same specificity and affinity as the analyte.

In heterogeneous specific binding assays described in the technical and patent literature, the receptor or other assay reagent of the specific binding reaction is often immobilized on a solid phase. Immobilization of the reagents is required to separate the bound components (for example an analyte bound to a receptor) from the unbound components.

The various methods by which a receptor or other reagent can be immobilized on a solid phase include adsorption, absorption or covalent bonding. However, many of the solid phase supports used in such assays are not inert and may sequester proteins and other substances from the sample by non-specific binding. Although glass is a relatively inert substrate, generally it has been found to be unsatisfactory for use in solid phase binding assays. See, for example U.S. Pat. No. 3,790,653 for a discussion of inadequacies of glass substrates.

Recently, however, procedures have been described for immobilizing an essentially soluble immunocomplex of a reagent and antiserum to the reagent on an inert glass fiber solid phase support. These procedures are disclosed in U.S. Pat. No. 4,517,288, incorporated by reference herein.

In these immunological immobilization procedures, soluble immunocomplexes are prepared by combining at least two immunochemically reactive substances with one another in solution. At least one of such immunochemically reactive materials is selected for its immunochemical specificity for an analyte of interest. For example, if the soluble immunocomplex is to be used in an immunoassay for the detection of thyroid stimulating hormone (TSH), then one component of the immunocomplex is selected for its immunochemical specificity for TSH. A typical example would be an antibody with specificity for TSH, i.e., an anti-TSH antibody. The second component of the immunocomplex could comprise an antibody preparation directed against the anti-TSH antibody. Antiserum to anti-analyte antibodies, for example to mouse anti-TSH antibodies, can be prepared by injecting purified mouse immunoglobulin G (IgG) into a host animal (i.e., goat), and thereafter harvesting the antiserum to the mouse IgG. The mouse anti-TSH antibody and the goat antiserum to mouse IgG are thereafter worked up as standard stock solutions.

Having prepared these stock solutions, a portion of each is combined in a buffered medium, The resulting immunocomplex, in an appropriate volume of buffer, may be spotted onto a delimited area of a glass fiber filter. Alternatively, the two components of the immunocomplex may be applied to the filter as separate buffered solutions and allowed to react in situ. In both instances, the point of application of the immunocomplex defines a reaction zone within the solid phase. The applied immunocomplexes become adsorbed and entrapped within the interstices of the beds of fibers within the glass fiber filter. The method of application can include dispensing of the immunocomplex solution with a manual or automated pipette, or with other automated equipment including assay analyzer instruments. Subsequent to application of the immunocomplex to the solid phase and the elapse of a suitable incubation period, the solid phase is dried under controlled conditions thereby yielding a stable reactive reagent which can be used in any one of a number of solid phase specific binding assay protocols.

Immunological immobilization, although useful in a variety of assay formats, has been noted to include a number of inherent disadvantages. Such factors as temperature, salt, pH and protein concentration have an influence on the formation of the double immunocomplex. These conditions can be difficult to optimize in order to effectively form the double immunocomplex. The presence of the additional immunoglobulins on the filter (e.g., antiserum to anti-analyte antibodies) can lead to nonspecific binding of proteinaceous and other biological materials. This can significantly decrease the assay sensitivity and overall performance. Moreover, given the inherent variability of IgG preparations from separate immunizations of the same or different host animals, lot-to-lot variability in titer, purity, specificity and affinity of IgG preparations must be accounted for in manufacturing procedures. Similarly, variability in the production of solid phase reagents may be encountered due to the tendency of immunocomplexes to become inhomogeneously distributed within stock solutions. That is, such immunocomplexes, while substantially soluble, may not remain completely soluble and may undergo some settling out of solution over time. Even with periodic mixing of stock solutions, gravitational influences, temperature gradients and other physical influences can cause subtle inhomogeneities within solutions applied to the solid phase reagents. These inhomogeneous solutions, resulting from protein aggregations, can cause blockage of the manufacturing lines used to spot the immunocomplex on the solid phase and other difficulties.

Some specific binding assays have been automated. A majority of the currently available automated assay systems, however, allow the detection of only one analyte in each cycle. Thus, in order to analyze more than one analyte in a single sample, one must wait for the testing cycle of a first analyte to be completed before a second analyte in the same sample can be tested and quantified. For most automated instruments a cycle time is usually at least 40 minutes. Alternatively, the sample to be analyzed could be aliquoted into multiple testing samples and analyzed simultaneously to obtain the desired quantification information. This second approach not only requires a greater amount of the patient sample, but also necessitates additional capital expenditure in order to operate multiple analyzers simultaneously.

A limited number of random access enzyme immunoassay (EIA) systems utilize a unit dose concept in order to analyze more than one analyte in a given sample. In these systems, all the required reagents such as the immobilized antibody, antibody-enzyme or drug-enzyme conjugate and the substrate required for the generation of the signal, are packaged together in a single packet and each packet contains reagents sufficient for a single analysis. This single packet system is more expensive than bulk storage and packaging. The added expense reflects, for example, the cost of separately packaging each component required for an assay, specific requirements of the packaging material allowing maximum stability of the reagents, and the extra storage space needed for each unit dose. In addition, the time required for incubations at different steps of the assay causes the over-all time for generation of results to be longer for random access assay systems.

SUMMARY OF THE INVENTION

The present invention includes methods for immobilizing a plurality of specific binding assay reagents on a solid phase. A dendrimer-reagent solution containing one or more dendrimer-reagent preparations is provided. Each of the preparations contains a plurality of dendrimer-reagent complexes, each of the dendrimer-reagent complexes having a defined specificity for at least one analyte or for a receptor of the at least one analyte. The complexes are dendrimers coupled to a specific binding assay reagent. The dendrimers can be E5 or N5 dendrimers. The dendrimers can be coupled to the reagents by C—S linkage carried out by combining SIAB-labeled moieties with sulfhydryl-containing moieties or C—S linkage carried out by combining SMCC labeled moieties with sulfhydryl-containing moieties. Alternatively, the dendrimers can be coupled to the reagents by C—N linkage carried out by combining aldehyde-labeled moieties with unmodified dendrimers. The reagents can be, without limitation, antibodies, antibody fragments, specific binding proteins or analytes. The sample is added to the dendrimer-reagent solution to form an assay solution. A selected amount of an indicator or a labeled specific competitive reagent may be added to the assay solution. The specific competitive reagent can be a labeled analogue of the at least one analyte. An effective amount of the assay solution is applied to a solid phase under conditions effecting immobilization of the dendrimer-reagent complexes on a delimited area of the solid phase.

The present invention also includes methods for conducting specific binding assays to determine the concentration or presence of at least one analyte in a sample. A dendrimer-reagent solution containing one or more dendrimer-reagent preparations is provided. Each of the preparations contains a plurality of dendrimer-reagent complexes, each of the dendrimer-reagent complexes having a defined specificity for at least one analyte or for a receptor of the at least one analyte. The complexes are dendrimers covalently coupled to a specific binding assay reagent. The dendrimers can be E5 or N5 dendrimers. The dendrimers can be coupled to the reagents by C—S linkage carried out by combining SIAB-labeled moieties with sulfhydryl-containing moieties or C—S linkage carried out by combining SMCC labeled moieties with sulfhydryl-containing moieties. Alternatively, the dendrimers can be coupled to the reagents by C—N linkage carried out by combining aldehyde-labeled moieties with unmodified dendrimers. The reagents can be, without limitation, antibodies, antibody fragments, specific binding proteins or analytes. The sample is added to the dendrimer-reagent solution to form an assay solution. An effective amount of the assay solution is applied to a solid phase under conditions effecting immobilization of the dendrimer-reagent complexes on a delimited area of the solid phase. A selected amount of an indicator is applied under binding conditions to the delimited area of the solid phase. The amount of indicator bound to the solid phase is determined and correlated to the concentration or presence of at least one analyte in the sample.

The present invention also relates to methods for conducting specific binding assays using a competitive assay format to determine the concentration or presence of at least one analyte in a sample. A dendrimer-reagent solution containing one or more dendrimer-reagent preparations is provided. Each of the preparations contains a plurality of dendrimer-reagent complexes, each of the dendrimer-reagent complexes having a defined specificity for at least one analyte or for a receptor of the at least one analyte. The complexes are dendrimers covalently coupled to a specific binding assay reagent. The dendrimers can be E5 or N5 dendrimers. The dendrimers can be coupled to the reagents by C—S linkage carried out by combining SIAB-labeled moieties with sulfhydryl-containing moieties or C—S linkage carried out by combining SMCC labeled moieties with sulfhydryl-containing moieties. Alternatively, the dendrimers can be coupled to the reagents by C—N linkage carried out by combining aldehyde-labeled moieties with unmodified dendrimers. The reagents can be, without limitation, antibodies, antibody fragments, specific binding proteins or analytes. The sample and a labeled specific competitive reagent are added to the dendrimer-reagent solution to form an competitive assay solution. The specific competitive reagent can be a labeled analogue of the at least one analyte. An effective amount of the competitive assay solution is applied to a solid phase under conditions effecting immobilization of the dendrimer-reagent complexes on a delimited area of the solid phase. A selected amount of an indicator is applied under binding conditions to the delimited area of the solid phase. The amount of indicator bound to the solid phase is determined and correlated to the concentration or presence of at least one analyte in the sample.

The present invention includes methods for conducting specific binding assays in which all reagents are incubated together in solution prior to immobilization on a solid phase. A dendrimer-reagent solution containing one or more dendrimer-reagent preparations is provided. Each of the preparations contains a plurality of dendrimer-reagent complexes, each of the dendrimer-reagent complexes having a defined specificity for at least one analyte or for a receptor of the at least one analyte. The complexes are dendrimers coupled to a specific binding assay reagent. The dendrimers can be E5 or N5 dendrimers. The dendrimers can be coupled to the reagents by C—S linkage carried out by combining SIAB-labeled moieties with sulfhydryl-containing moieties or C—S linkage carried out by combining SMCC labeled moieties with sulfhydryl-containing moieties. Alternatively, the dendrimers can be coupled to the reagents by C—N linkage carried out by combining aldehyde-labeled moieties with unmodified dendrimers. The reagents can be, without limitation, antibodies, antibody fragments, specific binding proteins or analytes. The sample and a selected amount of an indicator are added to the dendrimer-reagent solution to form an assay solution. An effective amount of the assay solution is applied to a solid phase under conditions effecting immobilization of the dendrimer-reagent complexes on a delimited area of the solid phase. The amount of indicator bound to the solid phase is determined and correlated to the concentration or presence of at least one analyte in the sample.

DETAILED DESCRIPTION

Figure 1:
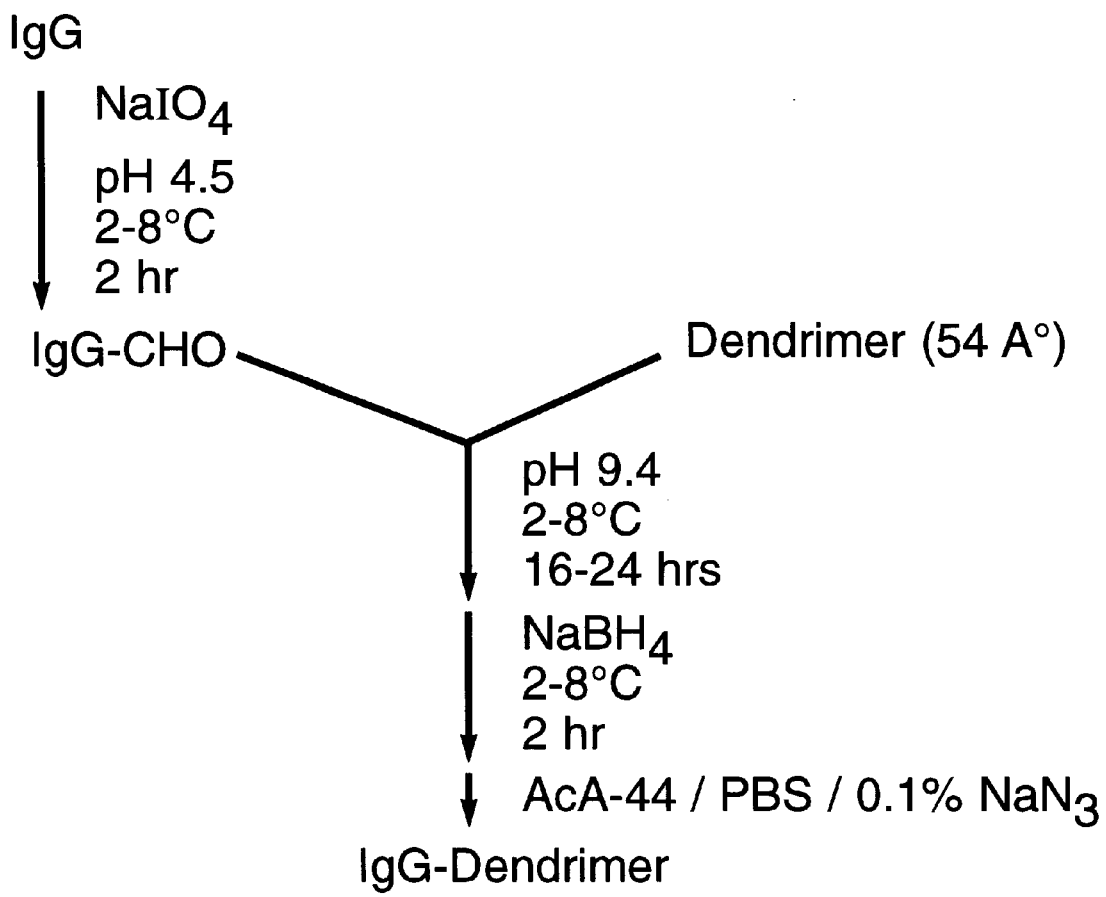
FIG. 1 is a schematic representation of the Schiff base chemistry for production of C—N linkages in dendrimer-reagent complexes, using as an example an antibody (IgG) reagent.

Starburst™ dendrimers (manufactured by The Dow Chemical Company) are polymers of spherical or other three-dimensional shapes that have precisely defined compositions and that possess a precisely defined molecular weight. The dendritic (tree-like) configuration derives from a structured branching wherein individual branches radiate out from a nucleus, or core region. The polyvalent core is covalently bonded to at least two ordered dendritic branches that extend through at least two tiers, or generations. The outermost tier or generation may be derivatized to terminate in functional groups that may be chemically reactive with a variety of other molecules. Thus, dendrimers are unitary molecular assemblages that possess three distinguishing architectural features, namely (a) an initiator core, (b) interior layers (generations) composed of repeating units radially attached to the initiator core, and (c) an exterior surface of terminal functionality attached to the outermost generation.

The size, shape and reactivity of a dendrimer can be controlled by the choice of the initiator core, the number of generations employed in creating the dendrimer, and the choice of the repeating units employed at each generation. Depending on the number of generations employed, dendrimers of discrete sizes are readily obtained. In addition, chemical modification of all or a portion of the surface moieties may create new surface functionalities appropriate for particular diagnostic or therapeutic operations. Generally spherical dendrimers of configurations suitable for use in the present invention are disclosed in U.S. Pat. No. 4,507,466 and U.S. Pat. No. 4,568,737, incorporated by reference herein. Alternatively, dendrimers of non-spherical configuration, such as those disclosed in U.S. Pat. No. 4,694,064, incorporated by reference herein, may be adapted for use in the present invention. Preferably, the dendrimers have an outer functionalized surface having amine-terminated functional groups. An E5 dendrimer is a fifth-generation, ethylenediamine core particle having 128 amine-terminated end (surface) groups and a molecular weight of 28,826. E5 has an estimated particle diameter of 70 Å. An N5 dendrimer is a fifth-generation ammonia core particle having 96 terminal amino groups and a molecular weight of 21,563. N5 has an estimated particle diameter of 53 Å. The amine-terminated end groups impart a net positive charge to the surfaces of such dendrimers under normal assay conditions.

Dendrimers can be synthesized as water soluble macromolecules through appropriate selection of internal and external moieties. See U.S. Pat. Nos. 4,507,466 and 4,568,737, incorporated by reference herein. Dendrimers may be conjugated with various pharmaceutical materials as well as with various targeting molecules that may function to direct the conjugates to selected body locations for diagnostic or therapeutic applications. See for example, WO 8801178, incorporated by reference herein. Starburst dendrimers have been used to covalently couple synthetic porphyrins (e.g., hemes and chlorophyll) to antibody molecules as a means for increasing the specific activity of radiolabeled antibodies for tumor therapy and diagnosis. Roberts, J. C. et al., Using Starburst Dendrimers as Linker Molecules to Radiolabel Antibodies, *Bioconjug. Chemistry* 1: 305–308 (1990).

Specific binding assay reagents may be attached to dendrimers by the formation of carbon-sulfur (C—S) linkages. Such C—S linkages are performed by derivatizing dendrimers with sulfosuccinimidyl-[4-iodoacetyl] aminobenzoate (sulfo-SIAB) or with succinimidyl 4-[N-maleimidomethyl] cyclohexane-1-carboxylate (SMCC) and combining the derivatized dendrimers with sulfhydryl-containing assay reagents. Alternatively, the specific binding assay reagents may be attached to the dendrimers by the formation of carbon-nitrogen (C—N) linkages or carbon-oxygen (C—O) linkages. See U.S. patent application Ser. No. 08/021,928, incorporated by reference herein. Dendrimer surface functional groups in addition to amino terminal groups include hydroxy, mercapto, carboxyl, alkenyl, allyl, vinyl, amido, halo, urea, oxiranyl, aziridinyl, oxazolinyl, imidazolinyl, sulfonato, phosphonato, isocyanato and isothiocyanato. Various known chemistries are usable with this wide range of surface functional groups and are useful for attachment of assay reagents to such functional groups.

Applicants have discovered that dendrimers can be used in place of antiserum to facilitate immobilization of assay reagents on the solid phase. That is, dendrimers can be covalently coupled to assay reagents such as antibodies or even relatively small molecules and then immobilized on various solid phases. In comparison to immunological immobilization, immobilization utilizing dendrimer complexes presents a number of distinct advantages. First, dendrimers can be consistently manufactured to retain lot-to-lot uniformity because of their precise polymer chemistries. These parameters can be uniformly maintained over different manufacturing lots. Second, the dendrimers can be manufactured to be water soluble such that the dendrimer-reagent conjugates remain in solution and maintain solution homogeneity over time. This eliminates lot-to-lot nonuniformity due to inhomogeneous distribution of immunological conjugates in solution. Third, the chemistries for attachment of reagents to the dendrimers are well characterized and are not subject to the variations inherent in associations of antisera and antibody binding substances. Antisera are subject to variations in affinity, specificity, and immunoglobulin purity, none of which are encountered during production of dendrimer-reagent conjugates.

In summary, dendrimer-based solid phase reagents are readily prepared having substantial lot-to-lot uniformity. Moreover, since stock or commercial solutions of dendrimer conjugates retain homogeneity over substantial periods of time, it is possible for end users of commercial assay instruments to prepare these solid phase reagents on site. The use of freshly prepared solid phase reagents further eliminates additional variables that may enter into distribution and commercial use of pre-prepared solid phase reagents, such as changes due to long term storage, temperature of storage, and other storage variables.

While dendrimer-reagent complexes are useful for preparation of various solid phase reagents in immunoassays and other assays, the applicants have found a particularly useful application of such complexes in use with glass fiber filter substrates and radial partition assays. Radial partition immunoassay as disclosed in Giegel et al., Clin. Chem. 28:1894–98 (1982) and in U.S. Pat. No. 4,517,288 is an assay procedure in which all steps are conducted directly on a solid phase. Antibodies or other reagents are immobilized on a small area of glass fiber filter paper. Various calibrators containing known amounts of an analyte to be detected or various unknown samples potentially containing such an analyte are then allowed to react with this immobilized receptor. Following appropriate additions of labeled analogues or other labeling reagents, excess reagents are removed from the center area of the filter paper by application of a wash fluid. In the case of an enzyme immunoassay, the wash fluid may contain the substrate for the enzyme, thus initiating the enzyme reaction simultaneously with the wash step. Preferably the action of the enzyme on the substrate generates a fluorescent signal. The enzyme activity in a part of the center area is then quantifiable by front-surface fluorometry. Depending on the assay format, i.e., direct binding assay or competitive assay, the rate of fluorescence is directly or inversely proportional to the concentration of analyte in the sample.

It is preferred that the solid phase present a relatively "inert" surface. That is, the surface should be relatively nonreactive with biological materials, particularly with respect to nondiscriminate adsorption of proteinaceous materials. In the preferred embodiments of this invention, the physical form of the solid phase is such that the interstices or pores within the solid phase are sufficiently small such that the reaction fluids are retained and transported by capillary action. On the other hand, the solid phase pores or interstices should not be so small so as to retain undesirable components that might give rise to false positive signals.

The solid phase is advantageously composed of a mat of compressed fibers, such as glass or synthetic fibers or relatively inert cellulosic materials. The solid phase also may be constructed of other porous constituents such as sintered glass, ceramics and synthetic polymeric materials. Glass fiber filter paper is the preferred solid support of the present invention because of its inert characteristic and because of its ability to adsorb the soluble complexes of this invention in quantities sufficient for quantitative evaluation of assay reagents. The surfaces of the glass fibers may carry a net negative charge, which facilitates adsorption of dendrimers having substantially positively charged surfaces under assay conditions, i.e., dendrimers with amine terminal surface groups. In a preferred embodiment, "tabs" as marketed by Baxter Diagnostics Inc. are assembled from GF/F glass filter paper distributed by Whatman Inc. and snap-fit plastic tab parts as discussed below. Generally the dendrimer-reagent complexes are applied to the center areas of such tabs in an appropriate buffer solution. Generally such buffers should include surfactants, analyte-free serum albumin and a preservative such as sodium azide. The dendrimer-reagent complexes of this invention, once adsorbed onto a suitable solid phase, can be used in a wide variety of analytical protocols for analysis of a variety of biological materials. For example, dendrimer-receptor complexes may be useful for immunoassay of blood or urine for the presence of therapeutic drugs, natural or synthetic steroids, hormones, enzymes, antibodies and other analytes of interest.

Therapeutic agents that can be analyzed in such protocols include without limitation digoxin, dilantin, phenobarbital, theophylline, gentamicin, quinidine, and the like. Solid phases prepared in the foregoing manner can also be used in immunoassays for the detection of steroids such as cortisol, aldosterone, testosterone, progesterone, and estriol or serum protein such as ferritin. Hormone levels are also capable of determination through the use of solid phase complexes of the present invention. These hormones include without limitation thyroid hormones such as tetraiodothyronine (T4) and triiodothyronine and thyroid stimulating hormone (TSH); peptide hormones such as insulin, corticotropin, gastrin, angiotensin, and proangiotensin; and polypeptide hormones such as thyrotropin, somatotropin and human chorionic gonadotropic hormone (HCG). Other applications of the complexes of the present invention include assay of relatively small molecules involved in metabolism, i.e., folate, to assay of polypeptide antigens and antibodies associated with infectious disease, i.e., antigens and antibodies associated with HIV, hepatitis, CMV, syphilis, Lyme disease agents, and numerous other infectious agents.

The dendrimer-reagent complex/solid phase preparations of the present invention are applicable to a variety of specific binding assay formats. For example, various direct-binding assays may be employed with these reagents. In such assays, receptors such as antibodies or binding proteins are covalently coupled to the dendrimers. The immobilized dendrimer-receptor complexes are contacted with a sample containing the analyte of interest and the complex is immobilized on the solid phase. Following immobilization of the complex, the solid phase is washed and then contacted with an indicator. The term "indicator" in the context of this invention means a labeled conjugate. The conjugate comprises an antibody, antibody fragment, binding protein or analyte depending on assay format, and the label is a fluorescent, enzymatic, calorimetric, radiometric or other labeling molecule that is associated either directly or indirectly with the conjugate. The label may comprise an enzymatic compound that produces fluorescence upon contact with a substrate. The extent to which the indicator is present on the solid support can be correlated with the amount of unknown analyte as disclosed, for example, in Tijssen, P., *Laboratory Techniques in Biochemistry and Molecular Biology*, Practice and Theory of Enzyme Immunoassay, pp. 173–219 (Chapter 10) and pp. 329–384 (Chapter 14), Elsevier Science Publishers, Amsterdam, The Netherlands, 1985.

The dendrimer/reagent complexes also may be used in competitive assay formats. In such formats, the complexes are mixed with a sample presumably containing such analyte and with a specific competitive reagent. The specific competitive reagent may be a labeled analogue of the analyte. The complexes are then immobilized on a solid phase. In this embodiment, the labeled analogue competes with the sample analyte for binding to a receptor. The amount of label bound to the solid phase after washing provides an indication of the levels of analyte in the sample. That is, the amount of label bound to the soluble phase is inversely proportional to the amount of analyte in the sample.

Various instruments are available for applying the dendrimer-reagent conjugates and various other binding assay reagents to a solid phase, washing, and reading the amounts of indicator bound to the solid phase. In a preferred embodiment, the solid phase comprises the glass fiber filter tabs as described above, and the instrument comprises the Stratus® Immunoassay System, available from Baxter Diagnostics Inc. This instrument is a batch-processing bench-top instrument, described by Giegel et al., Clin. Chem. 28:1894–98 (1982). The instrument is adapted to process tabs in the radial partition immunoassay format, which format is also described in Giegel et al. The instrument includes fluid dispensers for sample, conjugate and substrate washes. Microprocessor-controlled stepping motors aspirate and dispense required aliquots of reagents. All timing and operational aspects of the dispensers are predetermined by a program routine within the analyzer. The instrument also includes a tab transport system, heated platens with temperature monitoring, sample and reagent fluid pumps, a read station, data processing, and means for tab disposal. For quality control, the instrument microprocessor control program periodically verifies critical operating conditions such as reference voltages, temperatures, and dispensing settings, and flags for out-of-limit values.

Dendrimer-coupled antibodies have a very strong affinity for the glass fiber solid phase used in the Stratus® immunochemistry analyzers. In the spotting buffer (pH 8.0), the tab has a net negative charge whereas the dendrimer or dendrimer-coupled antibody has a net positive charge, due to the presence of a very large number of free amino groups. In fact, the opposite charge interaction of the dendrimers and glass fiber solid phase can be so strong that the dendrimer-coupled antibodies localize at the point of application on the solid phase and do not spread sufficiently to create a spot size of the desired diameter. Current Stratus® optics require a spot size of about 10 mm diameter for optimum detection of the reaction in an approximately 8 mm reaction zone. To compare different data sets generated with the Stratus® system, it is important to have a uniform spot size. It was found that addition of polylysine (molecular weight 22K) or free dendrimers (4th or 5th generation) helped in increasing the spot size on the glass fiber solid phase and, surprisingly, also amplified the signal. However, if the concentration of free dendrimers or polylysine is too high, the number of sites on the glass fiber can become filled by the free dendrimers or polylysine, preventing the dendrimer-coupled antibodies from binding to the solid phase. Therefore, amounts of free dendrimers or polylysine present in the spotting buffer should be routinely titrated prior to immobilization of the specific dendrimer-coupled antibody solution in order to optimize the spot size on the solid phase.

Studies using ammonia core dendrimers showed that to obtain signals comparable to the double-antibody system, at a reasonable protein concentration, fifth generation dendrimers were most preferable for coupling. Lower generation dendrimers gave about 40% of the signal as compared to that with the fifth generation dendrimers. Higher generation dendrimers gave about the same signal as that obtained for the fifth generation particles but produced much larger aggregates. Because the size and shape of the particles were found to influence some performance parameters, fifth generation dendrimers were preferred in the assays.

In a preferred embodiment, dendrimer-coupled antibody is allowed to bind in solution to the analyte of interest. Due to conformational freedom, solution phase receptor-analyte reactions generally are subject to fewer steric restrictions and requirements that would be present in a solid phase reaction format. This leads to faster attainment of kinetic equilibrium than if the receptor analyte reaction were performed on a solid phase. The solution containing the dendrimer-coupled antibody-antigen complex is then spotted on a glass fiber solid phase, such as a Stratus® tab, and the tab is used in a specific binding assay format. The antibody-antigen complex and any excess dendrimer-coupled antibody are captured by the solid phase, and the non-specifically bound materials are washed away under the standard Stratus® wash conditions. A detector specific for the presence of the analyte, such as an enzyme-labeled anti-analyte antibody conjugate, and an indicating substrate are applied to the reaction zone. The signal generated by the assay is directly dependent on the concentration of the analyte and is not affected by the presence of any non-specific reagents.

In an alternative embodiment, dendrimer-coupled antibody is placed in solution with the analyte of interest and also with a labeled specific competitive reagent, such as an analog of the analyte. The solution containing the dendrimer-coupled antibody, analyte and competitive reagent is then spotted on a glass fiber solid phase, such as a Stratus® tab, and the tab is used in a specific binding assay format. Excess unbound competitive reagent is washed away under the standard Stratus® wash conditions. The signal generated by the assay is inversely proportional to the concentration of the analyte.

In another embodiment, dendrimer-coupled antibody is allowed to bind in solution to the analyte of interest in the presence of an indicator. An effective amount of the solution containing the dendrimer-coupled antibody, analyte and indicator is spotted onto a glass fiber solid phase. The solid phase is subsequently washed under appropriate wash conditions, and the amount of indicator coupled to the solid phase is determined.

Two ways to facilitate the binding of the maximum amount of the analyte in a Stratus® cycle, and thus assist in driving the equilibrium to completion in the shortest possible time, are to increase the antibody concentration and to increase the conjugate concentration. In the present invention these two variables can be adjusted in order to significantly shorten the necessary reaction time.

The solid phase used in the present invention may contain a population of dendrimer-reagent complexes that have specificity for more than one analyte. That is, the solution may contain at least two different dendrimer-reagent preparations, each preparation having specificity for a selected analyte. These are termed mixed antibody dendrimer solutions. The dendrimer-reagent complexes of the preparations are intermixed and applied to a delimited area of the solid phase to form a reaction zone useful for analysis of multiple analytes. Alternatively, the solution or solid phase may contain a single dendrimer-reagent preparation where each dendrimer-reagent complex of the preparation has specificity for at least two different analytes. These are called multiple-specificity dendrimer solutions or solid phases.

The mixed antibody dendrimer solutions and the multiple-specificity dendrimer solutions of the present invention can be especially useful in cases where a patient sample is to be assayed for a specific diagnosis using a panel of tests where each test is an indication of a different stage of a clinical symptom. For example, a cardiac panel might require testing for creatine kinase isozyme MB (CKMB), troponin, myoglobin and digoxin. A cancer markers panel might test for carcinoembryonic antigen (CEA), alpha-fetoprotein (AFP) and human chorionic gonadotropin hormone (HCG).

The invention will be further understood with reference to the following illustrative embodiments, which are purely exemplary, and should not be taken as limiting the true scope of the present invention as described in the claims.

EXAMPLE 1

Preparation of Solid Phase Supports (Tabs)

Solid phase supports used in the present experiments comprised "tabs" as used with the Stratus® analyzer instrument or the Stratus® II analyzer instrument, both marketed by Baxter Diagnostics Inc. These tabs are assembled from 1-in. (2.5 cm)-wide rolls of GF/F glass filter paper (Whatman Inc.) and snap-fit plastic tab parts, as disclosed in Giegel et al., Radial Partition Immunoassay, *Clin. Chem.* 28: 1894–98 (1982). Appropriate concentrations of dendrimer solutions, antibody solutions or other protein or control solutions are made up in spotting buffer. The spotting buffer composition may be varied to accommodate particular experimental or manufacturing parameters. Generally the spotting buffer may comprise, for example, 20 mM–200 mM Tris, pH 7.0–9.0, a non-ionic surfactant such as Zonyl® FSN (E. I. DuPont DeNemours & Co., Cat. No. CH 7152S) in a concentration range of 0.1%–1.0%, bovine serum albumin (BSA) at 0.5%–4.0% and 0.1% sodium azide. Preferably the spotting buffer comprises 30–100 mM Tris, pH 7.0–8.5, 0.1%–0.5% Zonyl® FSN, 1.0%–3.0% BSA and 0.1% sodium azide. Most preferably the spotting buffer comprises 50 mM Tris, pH 8.0, 0.1% Zonyl® FSN, and 2.0% BSA. Fluorinated surfactants (e.g. 3M Cat. No.'s FC 171 and FC 170C) and other appropriate surfactants known to the skilled artisan may be substituted for Zonyl® FSN. The spotting buffer also comprises 0.01–0.1% polylysine (molecular weight 15,000–30,000; sigma Cat. No. P7890) or free dendrimers (fourth generation or higher). Preferably, the spotting buffer comprises 0.03–0.05% of a fifth generation free dendrimer. Other equally charged molecules known in the scientific literature may be substituted for the free dendrimer.

Aliquots of 76 $\mu$l of a selected solution are spotted onto the centers of blank tabs. After an appropriate incubation period of the dendrimer-coupled antibody, the analyte, conjugate and substrate wash are applied to the wet tab. The tabs may be stored at 2°–8° C. until used. Spotting of the solutions on the tabs may be carried out manually with a pipetting device or may be carried out with automated manufacturing procedures. Alternatively, the tabs may be spotted and processed by the Stratus® II instrument itself, following appropriate programming of machine parameters to apply selected aliquots of stock solutions to the centers of tabs.

EXAMPLE 2

Preparation of IgG-Dendrimer via Schiff Base Linkage

A flow diagram of the following procedure is depicted in FIG. 1. An IgG concentrate solution consisting of 4–5 mg IgG/ml in pH 4.5 acetate buffer (0.1 M NaOAc/0.1 M NaCl) is prepared and chilled on ice. A ⅔ volume of chilled, 0.1 M NaIO$_4$ in pH 4.5 acetate buffer is added to the IgG solution and the combined IgG/NaIO$_4$ solution is incubated in the dark for 2 hrs. at 2°–8° C. Ethylene glycol at 10 $\mu$l/ml of original IgG concentrate solution is added and the incubation is continued for an additional ½ hr. at 2°–8° C. The resulting solution of IgG-aldehyde derivative (IgG-CHO) is desalted by passage over an appropriately sized column of Sephadex G-25 equilibrated with pH 4.5 acetate buffer. Protein fractions are collected and pooled and the concentration of IgG-CHO is determined spectrophotometrically at 280 nm using an extinction coefficient of 1.48 ml mg$^{-1}$·cm$^{-1}$. The aldehyde content of the periodate-oxidized IgG may be quantified using the aldehyde-modifying reagent Purpald (Aldrich, Cat. No. 16-289-2) with appropriate concentrations of formaldehyde as calibrators.

Dendrimers (about 50–70 Å particle size) in aqueous solution (Michigan Molecular Institute, Midland, Mich.) are added to the desalted IgG-CHO solution at a 3:1 molar ratio of dendrimer:IgG-CHO. The combined dendrimer/IgG-CHO is buffer exchanged into 0.1 M sodium carbonate buffer, pH 9.4, and the solution volume is adjusted to provide a final IgG concentration of approximately 1.0 mg IgG/ml. The solution is then incubated at 2°–8° C. for 16–24 hrs. Then, a volume of freshly prepared NaBH$_4$ solution (4 mg/ml in water) equal to 1/20 of the volume of the dendrimer/IgG-CHO reaction mixture is slowly added and incubated at 2°–8° C. for an additional 2 hrs. The resulting solution is clarified, if necessary, by filtration through a 0.22 $\mu$m filter. An appropriately sized column of polyacrylamide-agarose gel matrix (AcA-44 Ultrogel, IBF, Cat. No. 230161) is prepared and equilibrated in phosphate-buffered saline (PBS)/0.1% NaN$_3$. The final dendrimer/IgG-CHO reaction mixture is concentrated to a volume of less than 3% of the AcA-44 bed volume, then loaded onto the column and eluted at an appropriate flow rate. Fractions containing the first protein peak, which comprises the coupled IgG-dendrimer preparation (IgG-DEND), are pooled. The concentration of IgG in the IgG-DEND preparation is determined spectrophotometrically using an extinction coefficient of 1.48 ml·mg$^{-1}$·cm$^{-1}$ at 280 nm.

EXAMPLE 3

Preparation of IgG-Dendrimer via SIAB Linkage

Figure 2:
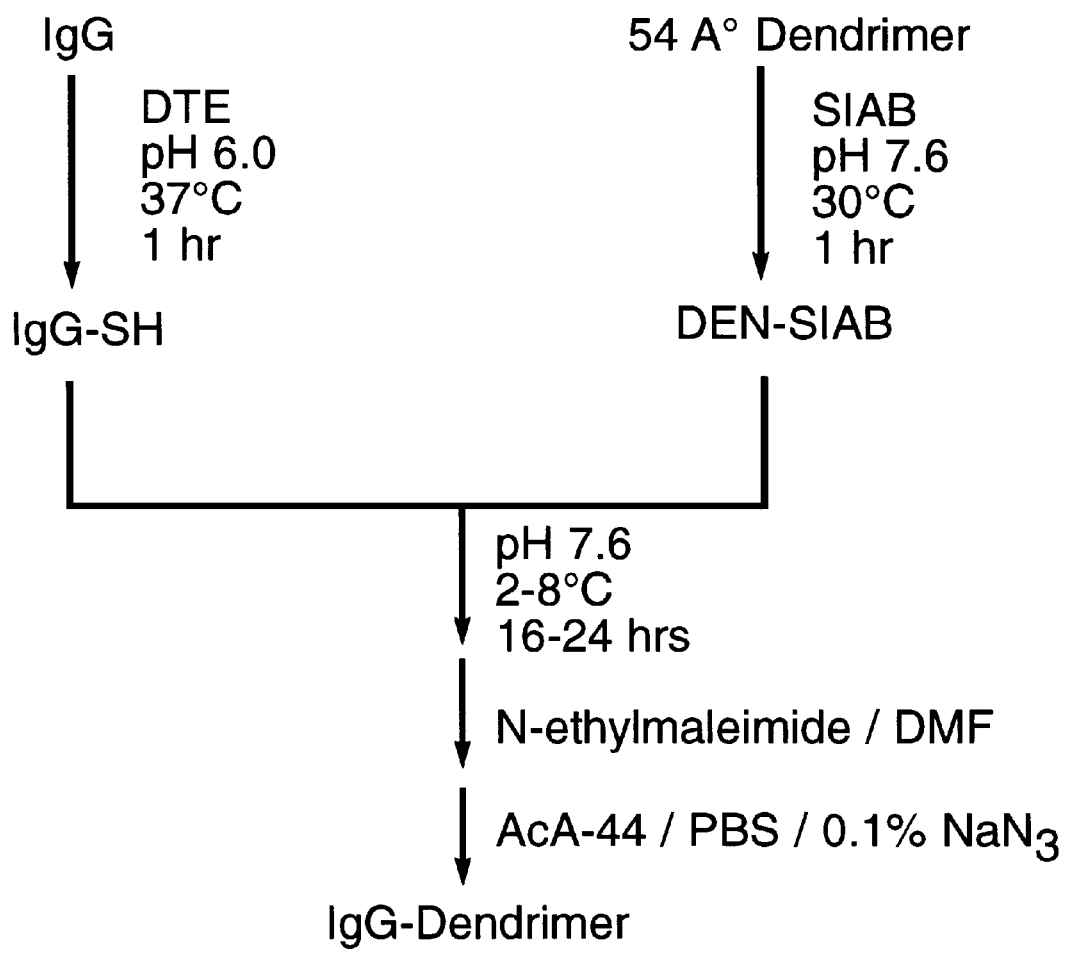
FIG. 2 is a schematic representation of the sulfosuccinimidyl-(4-iodoacetyl) aminobenzoate (SIAB)-based chemistry for production of C—S linkages in dendrimer-reagent complexes, using as an example an antibody (IgG) reagent.

A flow diagram of the following procedure is depicted in FIG. 2. A one-fifth volume of sodium phosphate buffer (0.5 M NaH$_2$PO$_4$, pH 7.1) is added to the vendor-supplied aqueous solution of 54 Å dendrimer (MMI, Midland, Mich.). The resulting solution is adjusted to pH 7.6 with 1 N HCl or 1 N NaOH. An appropriate volume of 15 mg/ml sulfo-SIAB in water is added to the dendrimer solution to equal a 20:1 molar ratio of sulfo-SIAB:dendrimer, then incubated at 30° C. for 1 hr. The resulting solution of SIAB-dendrimer derivative (SIAB-DEND) is loaded onto an appropriately sized column of Sephadex G-25 previously equilibrated with 0.1 M $NaH_2PO_4$, pH 7.6. Following elution at a flow rate of approximately 0.5 ml/min, the SIAB-DEND fractions are pooled and the concentration of SIAB-DEND is determined with fluorescamine, a fluorogenic reagent used for assay of primary amines, as described in Weigele et al., J. Am. Chem. Soc. 94: 5927 (1972) and in Udenfriend et al., Science 178: 871 (1972). Appropriate concentrations of underivatized 54 Å dendrimer are used as calibrators.

For preparation of sulfhydryl-IgG derivative (IgG-SH), a solution of 5 mg IgG/ml in reduction buffer (0.1 M $NaH_2PO_4$, 5 mm EDTA, pH 6.0) is prepared. Dithioerythritol (DTE) or dithiothreitol (DTT) is dissolved in reduction buffer at a concentration of 11.4 mg/ml. The DTE solution is added to the IgG solution in a volume equal to ⅕ of the volume of the 5 mg/ml solution of IgG, then incubated at 37° C. for 1 hr. The resulting IgG-SH solution is then desalted by passage over an appropriately sized Sephadex G-25 column, and the IgG-SH concentration and SH content determined with standard methods.

Finally, to prepare the IgG-DEND, the SIAB-DEND solution is combined with the IgG-SH solution at a 3:1 molar ratio of SIAB-DEND: IgG-SH, and then buffer-exchanged into sodium phosphate buffer (0.1 M $NaH_2PO_4$, pH 7.6). The solution is volume-adjusted to a final IgG concentration of approximately 5 mg/ml, then incubated at 2°–8° C. for 16–24 hrs. The reaction is stopped by addition of a ⅕₀ volume of quenching solution consisting of 10 mg/ml N-ethylmaleimide (NEM) in N,N-dimethylformamide (DMF) followed by an additional incubation at room temperature (23°–25° C.) for 2 hr. The quenched reaction mixture is clarified, if necessary, by passage through a 0.22 µm filter, then purified either by diafiltration (Amicon, YM-100) or by passage over an AcA-44 Ultrogel column as described in Example 2 above.

EXAMPLE 4

Coupling of Anti-hTSH Antibody (CA2) with Dendrimers

About 12 ml of ascites fluid containing approximately 60 mg of anti-hTSH (CA2) antibody was purified over a Q-Sepharose column (1.0×13.0 cm) using a gradient between 20 mM Tris, pH 8.5 and 20 mM Tris/0.3 M NaCl, pH 7.0 to yield 54 mg of the purified antibody protein. CA2 is on deposit at the American Type Culture Collection (ATCC) under Accession Number 1437. The antibody solution, containing 35 mg protein, was diluted with an equal volume of binding buffer (Bio-Rad) and purified over a Protein A column (1.0×6.5 cm, Bio-Rad AffiPrep) by absorbing the antibody to the column and then eluting the bound protein with 0.1 M sodium acetate-0.1 M sodium chloride, pH 5.0 to yield 26.0 mg of the antibody in solution.

The E5 dendrimer (MMI, Midland, Mich.) was iodoacetylated following the general procedure discussed in Example 3 above. A 20-fold molar excess of sulfo-SIAB was added to the aqueous dendrimer solution. Each dendrimer particle incorporated approximately 2.5 iodoacetyls.

The antibody solution (2.0 ml at 5.0 mg/ml) was reduced for 1 hour at 37° C. with DTE or DTT (0.23 ml of 4.5 mg/ml) in 0.1 M sodium phosphate-5.0 mM EDTA, pH 6.5 following the general procedure given in Example 3 above. After desalting over a G-25 column in the reduction buffer, the product showed the presence of about 10 sulfhydryls per IgG.

The reduced antibody was then coupled with the iodoacetylated dendrimer in a 1:3 molar ratio as described in the general coupling procedure set out in Example 3 above. Final product was purified either by diafiltration (Amicon, YM-100), or by passage over an AcA-44 column in PBS. The stoichiometry of dendrimers to antibody in the final purified product was found to be 1.0±0.3.

The E5-coupled antibody solution can be stored for at least one year at room temperature. Only about a 7% change in rates, as monitored for the calibrator F (containing 50 µIU/mL hTSH), occurred when the solution was stored for one year at room temperature.

EXAMPLE 5

Coupling of Anti-CKMB Antibody with Dendrimer

Purification of an antibody directed against creatine kinase isozyme MB (CKMB, Conan, ATCC Accession No. HB8939) was carried out over Q-Sepharose as described above in Example 3, producing about a 65% yield. The E5 dendrimer was challenged with a 20-fold molar excess of sulfo-SIAB to incorporate approximately 2.5 iodoacetyls per dendrimer. The antibody solution was reduced for 1 hour at 37° C. with DTE or DTT at pH 6.5 following the general procedure given in Example 3 above. After desalting over a G-25 column in the reduction buffer, the product showed the presence of about 8.5 sulfhydryls per IgG. Coupling of the derivatized E5 with the reduced IgG was carried out as described in the case of hTSH (Example 4). Purification of the final product was carried out either by diafiltration (Amicon, YM-100) or over an AcA-44 column prepared and eluted with PBS.

EXAMPLE 6

Figure 3:
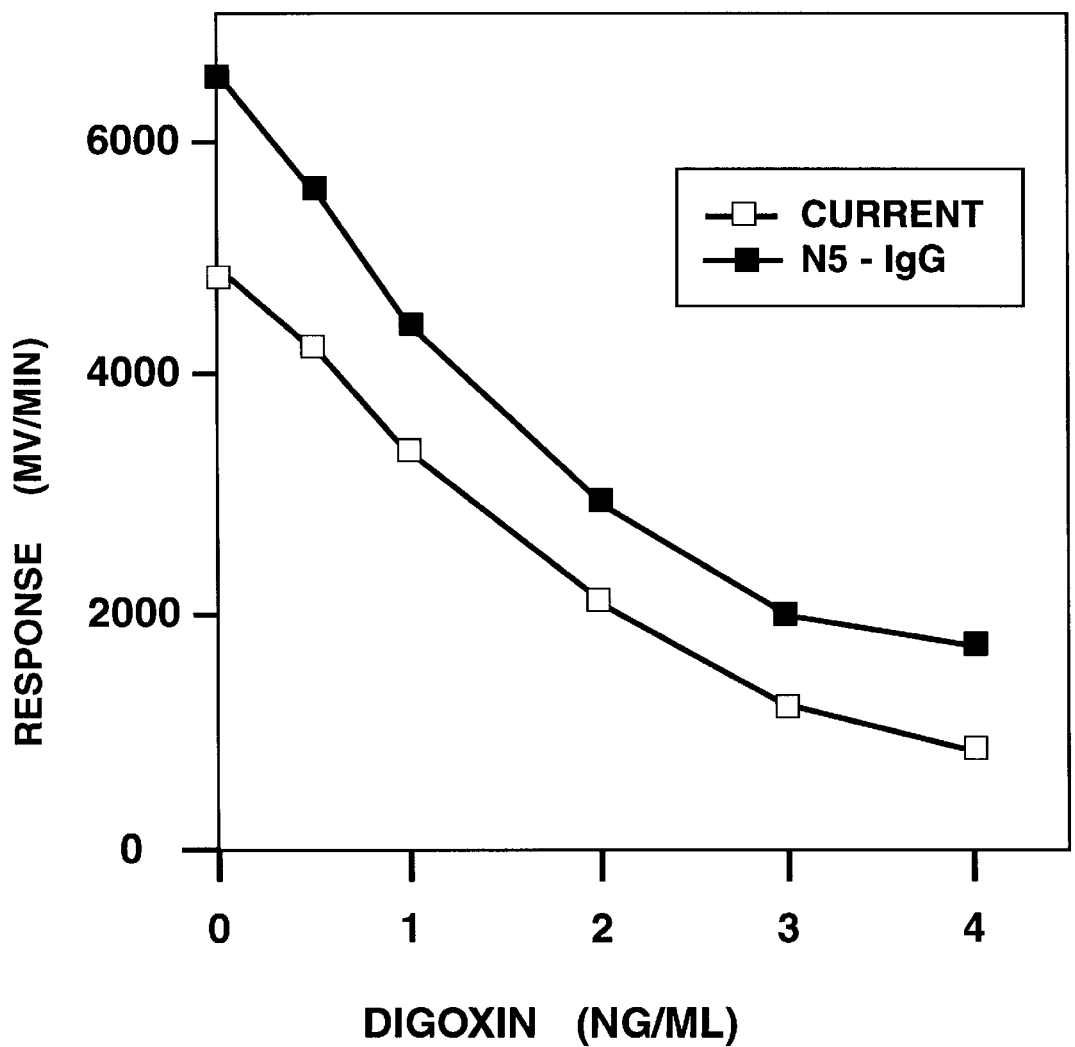
FIG. 3 depicts a comparison of the calibration curves of digoxin assays using the double antibody immunocomplex format and the dendrimer-coupled antibody format.

Comparison of Double-Antibody Complex Assay with Immobilized Dendrimer-Coupled Antibody Assay To confirm that dendrimer-coupled antibodies are effective in a radial partition assay format, a digoxin assay was chosen for evaluation. This assay was carried out in a sequential saturation format. In this format the sample containing the analyte was applied to dry tabs containing the immobilized antibody either as a double-antibody immunocomplex or as dendrimer-coupled antibody. After an appropriate interval, a substrate wash containing a conjugate, such as a labeled analog of the analyte, was applied to the tab. The signal generated on application of the substrate wash, as expected in a sequential saturation format assay, was inversely proportional to the analyte concentration. FIG. 3 depicts calibration curves for digoxin for a double-antibody assay and for a dendrimer-coupled antibody assay. In the double-antibody assay an anti-digoxin polyclonal antibody was immobilized by means of a goat anti-rabbit antibody to form a polyclonal double-antibody complex. In the dendrimer-coupled antibody assay, the anti-digoxin polyclonal antibody (purchased from Sigma) was coupled with N5 dendrimers and immobilized on the solid phase via the dendrimers. The antibodies were coupled to the dendrimers as in Example 3 above.

EXAMPLE 7

Preparation of a Solution of Several Dendrimer-Coupled Antibody Preparations A mixed solution containing two preparations of dendrimer-coupled antibodies, i.e., a preparation of E5-coupled antibodies against CKMB and a preparation of E5-coupled antibodies against hTSH, was prepared. The optimized working concentration was determined for each dendrimer-coupled antibody preparation in separate experiments on Stratus® II. For the CKMB and hTSH assays the optimized concentration of the dendrimer-coupled antibody was found to be 10 $\mu$g/ml. The optimized concentration for the tetraiodothyronine (T4) assay was found to be 0.56 $\mu$g/ml. A solution of the optimized protein concentrations was tested and stored in 50 mM Tris, 0.1% v/v FSN, 0.033% w/v unmodified E5, pH 8.0.

Also, a mixed solution was prepared containing three preparations of monoclonals specific for hTSH, CKMB and T4 coupled separately to E5 following the method described in Example 3 above. Identical calibration curves were generated for the specific analyte when the solution contained either single analyte-specific E5-coupled antibodies or a mixture of the three E5-coupled antibody preparations. Thus, the presence of non-specific E5-coupled monoclonals had no impact on the specific analyte-antibody reaction. Furthermore, as shown in Table 1 below, when a solution containing a mixture of analytes was tested, the concentration of the specific analyte detected was very similar whether the solution contained the specific E5-coupled antibody or the mixture of dendrimer-coupled antibody preparations. Thus, for the random detection of an analyte, a solution containing a mixture of dendrimer-coupled antibody preparations can be used instead of a number of solutions that would otherwise be required for this purpose.

on FPLC using a Superdex 200 (Pharmacia) column in PBS. The fractions containing IgG-E5 are pooled and the protein concentration is determined by BCA assay. In cases where a mixture of anti-T4, anti-CKMB and anti-hTSH is used for coupling, the dendrimer-coupled antibody solution is diluted to a total protein concentration of 10.3 $\mu$g/ml in 50 mM Tris, 0.1% FSN, pH 8.0 and tested on Stratus® II. The dendrimer-coupled antibody solution prepared from a mixture of anti-CKMB and anti-hTSH antibodies are diluted to a total protein concentration of 10 $\mu$g/ml in 50 mM Tris, 2% BSA, and 0.1% FSN, pH 8.0 for testing and storage.

EXAMPLE 9

Solution-Based Dendrimer-Coupled Antibody Assay

A stock solution of the dendrimer-coupled antibody was prepared in spotting buffer containing 50 mM Tris, 0.1% v/v Zonyl® FSN, 2.0% protease-free BSA and 0.03% of the free dendrimer, pH 8.0. Thirty-eight microliters of this stock solution was preincubated with 132 $\mu$l of a sample containing the analyte. The assay was performed on Stratus® II by aspirating and delivering 76 $\mu$l of this mixture onto a blank tab, as described in Example 1 above. After an appropriate interval, 20 $\mu$l of the appropriate alkaline phosphatase conjugate (0.75 $\mu$g/ml) were then delivered to each tab. The Stratus® instrument substrate probe then aspirated 70 $\mu$l of the substrate wash (pH 9.0 Tris buffer containing 1.0 mM 4-methylumbelliferyl phosphate, alkaline phosphatase inhibitor, stabilizers, blue dye, surfactant and 0.1% sodium

TABLE 1

RANDOM DETECTION OF MULTIPLE ANALYTES IN A SINGLE SAMPLE WITH A SINGLE TYPE OF DENDRIMER-COUPLED ANTIBODY OR A MIXTURE CONTAINING THREE TYPES OF DENDRIMER-COUPLED ANTIBODIES

| | CKMB | | hTSH | | T4 | |
|---|---|---|---|---|---|---|
| | SINGLE | MIXTURE | SINGLE | MIXTURE | SINGLE | MIXTURE |
| MV/MIN* | 1321.4 | 1461.3 | 3842.8 | 3806.9 | 1944.2 | 2223.4 |
| CONC.^ | 12.62 | 14.26 | 11.44 | 10.79 | 9.73 | 8.88 |

*Average of triplicates.
^Concentration determined from MV/MIN. Analyte concentration units are ng/ml, $\mu$IU/ml and $\mu$g/dl for CKMB, hTSH and T4 respectively.

EXAMPLE 8

Preparation of Multiple-Specificity Dendrimers

The dendrimers are iodoacetylated following the general procedure discussed in Example 2 above. A 20 to 50 fold molar excess of sulfo-SIAB is added to the aqueous dendrimer solution. Each dendrimer particle incorporates approximately 6–10 iodoacetyls.

A mixture of purified anti-CKMB and anti-hTSH antibodies in a 1:1 ratio (by weight) is reduced for one hour at 37° C. with DTT in the reduction buffer following the general procedure described in Example 3 above. After desalting over a G-25-column that was prepared and eluted with the reaction buffer, the product shows the presence of about 10 sulfhydryls per IgG.

The reduced antibody mixture is then coupled to the iodoacetylated dendrimer in a 1:5 to 1:10 molar ratio as described in the general coupling procedure set out in Example 3 above. The excess uncoupled antibody present in the final product solution is removed by gel filtration purification either by using an AcA-34 (or equivalent) column or azide) and released 20 $\mu$l and 50 $\mu$l sequentially to the tab. The signal thus generated was measured by front surface fluorometry in the Stratus® instrument and recorded in the instrument's memory, as described in Giegel et al., Clin. Chem 28: 1894–98 (1982).

The radial partition assay format described in Giegel et al. was used in all of the experiments. Calibrator solutions A, B, C, D, E and F were prepared either in normal human serum or in a Tris-buffered solution (pH 7.5) including BSA, stabilizer and 0.1% sodium azide as a preservative. Calibrator solutions A, B, C, D, E and F for hTSH contained concentrations of 0, 0.25. 0.75, 3, 12 and 50 $\mu$IU/ml, respectively; the calibrator solutions for CKMB contained concentrations of 0.0, 4.80, 11.60, 26.90, 61.10 and 127.80 ng/ml.

Figure 4:
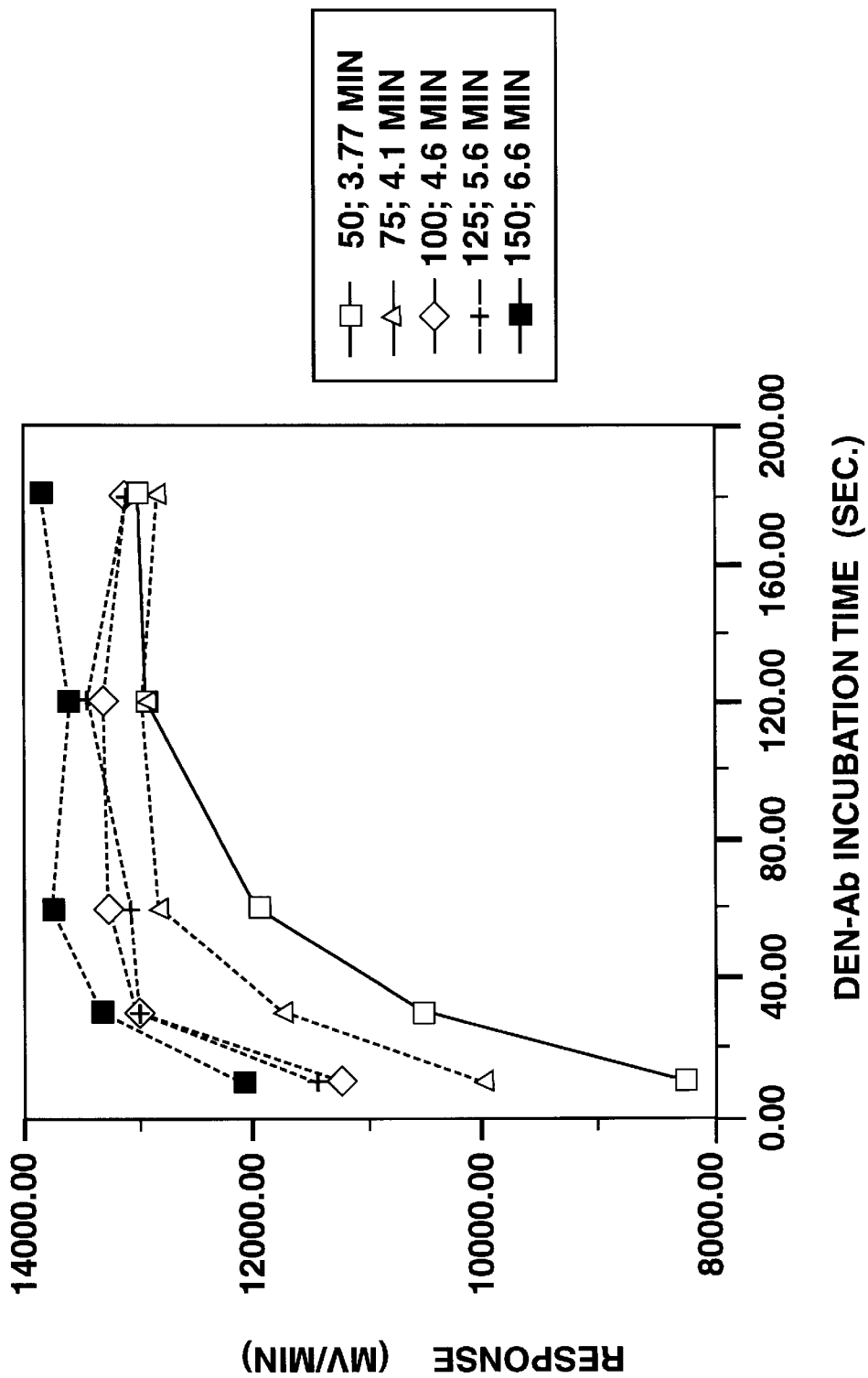
FIG. 4 depicts the effect of incubation time and concentration of dendrimer-coupled antibody on the signal response in a CKMB assay.

FIG. 4 shows that by increasing the dendrimer-coupled antibody concentration in a CKMB assay while keeping the conjugate incubation time fixed at 60 seconds, equilibrium was established very quickly (i.e. in less than 60 seconds), as monitored by the change in signal generated. Continued incubation beyond the initial increase in the signal did not significantly improve the signal. This shortening of the incubation time of the dendrimer-coupled antibody with the analyte has the advantage of making the overall assay completion time faster. The overall assay times are shown in Table 2.

TABLE 2

COMPARISON OF OVERALL ASSAY TIMES

| DEN-Ab INCUBATION<br>TIME (seconds) | TOTAL ASSAY<br>TIME (minutes) |
| --- | --- |
| 10 | 3.77 |
| 30 | 4.1 |
| 60 | 4.6 |
| 120 | 5.6 |
| 180 | 6.6 |

Figure 5:
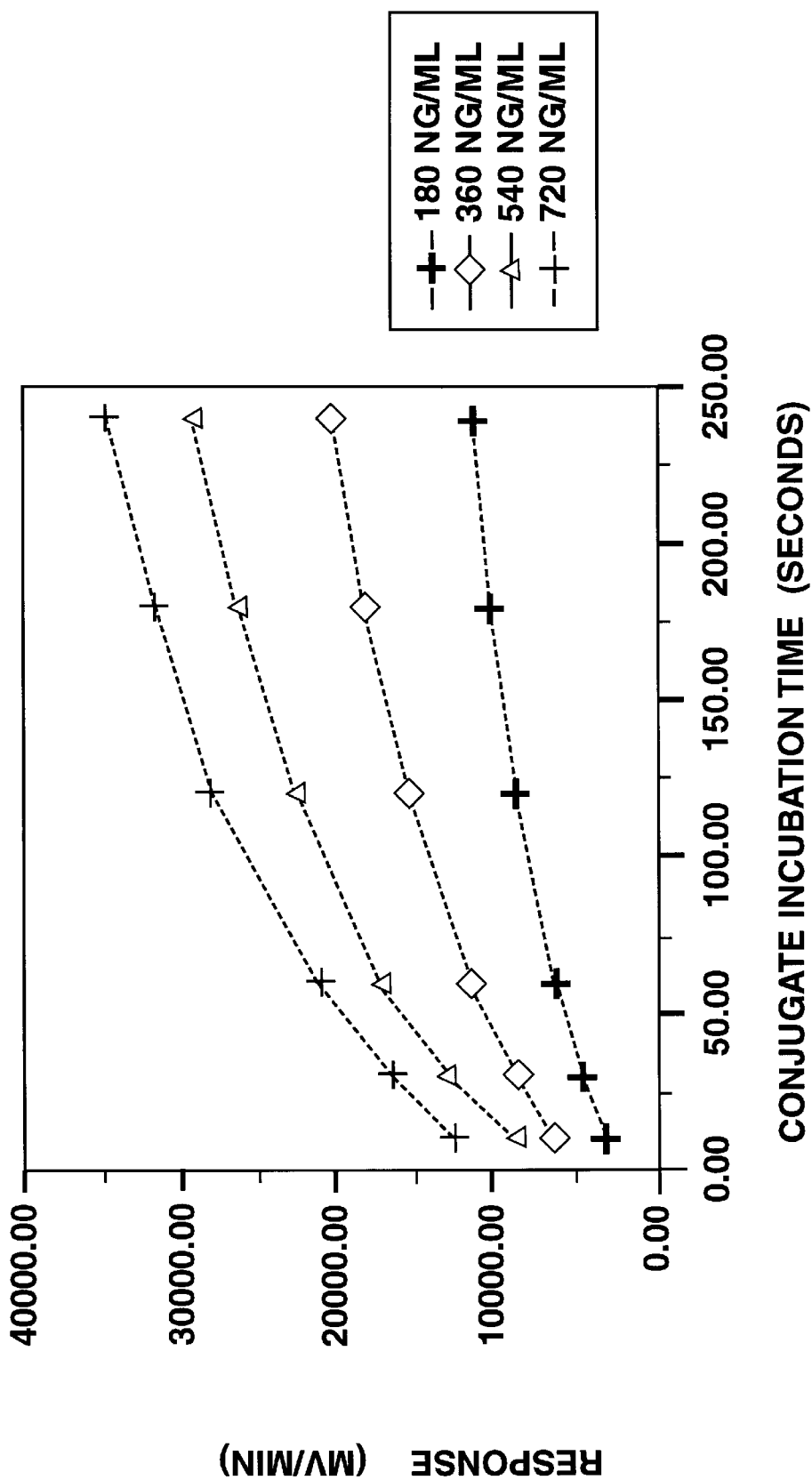
FIG. 5 depicts time dependent effect of varying the conjugate concentration and its effect on response of CKMB assay using the dendrimer-coupled antibody format.
Figure 6:
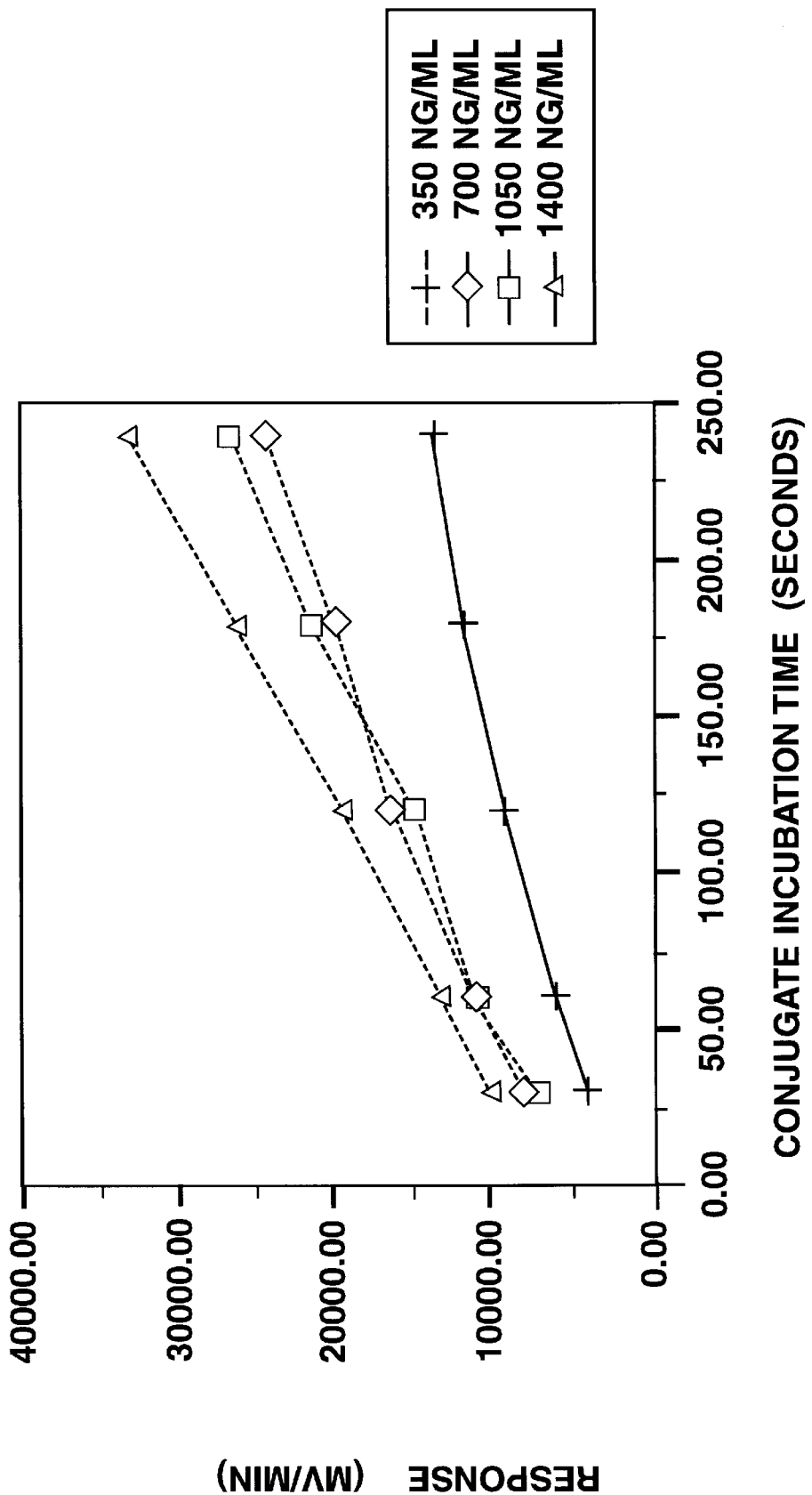
FIG. 6 depicts time dependent effect of conjugate concentration on response in hTSH assay.

Results for CKMB and hTSH assays using the methods of the present invention are depicted in FIGS. 5 and 6, respectively. FIG. 5 shows that by increasing the concentration of the conjugate in the CKMB assay, the maximum effect, as shown by the increase in the signal, was evident during the initial incubation periods of 100 seconds or less. Additional incubation time did not offer any significant advantage. FIG. 6 shows that for the hTSH assay, increasing the conjugate concentration seemed to increase the signal over a broader range of the incubation periods. FIGS. 4–6 also show that it was possible to manipulate the kinetics of the reaction by adjusting the times and concentrations of the dendrimer-coupled antibody as well as that of the conjugate.

Figure 7:
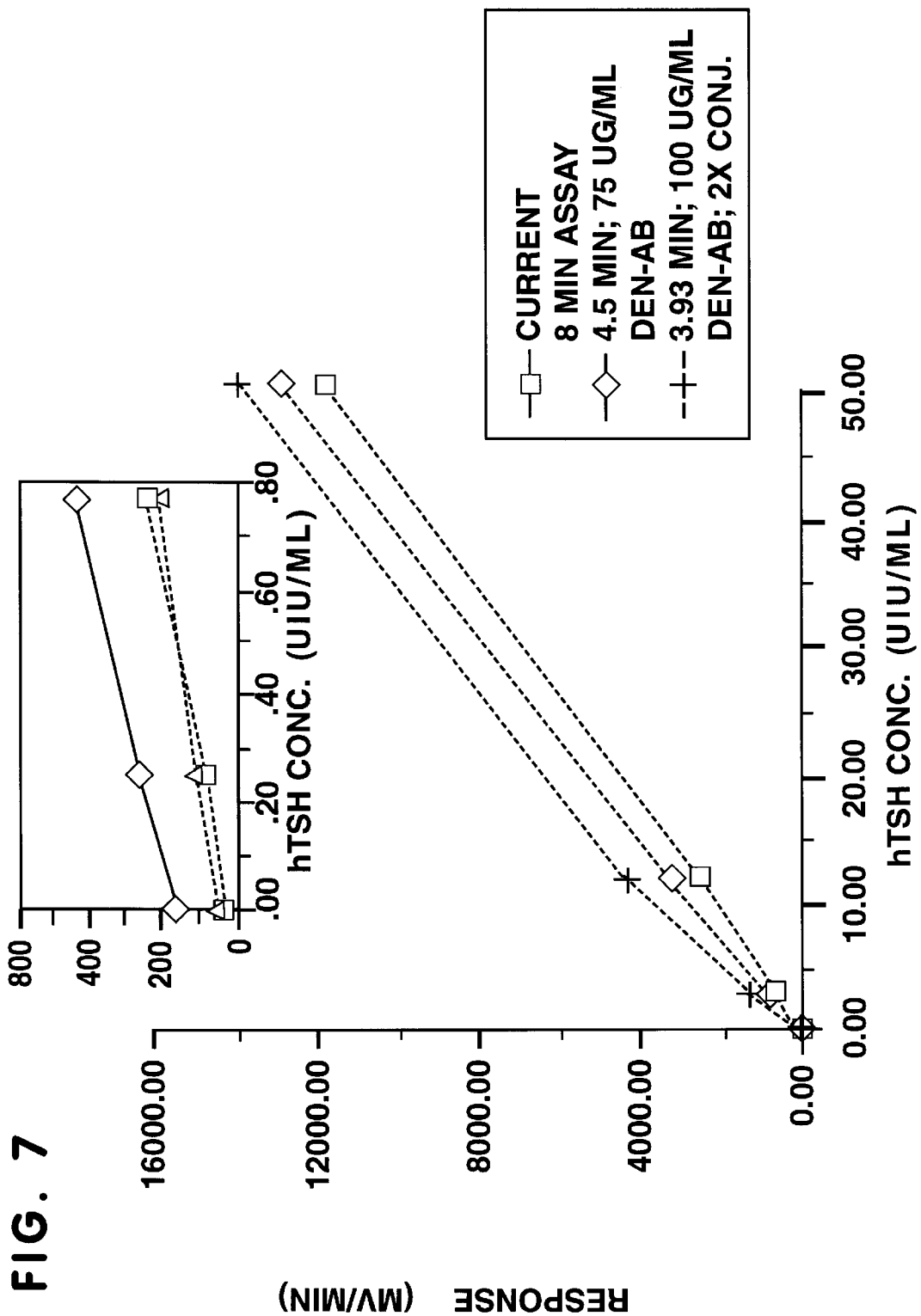
FIG. 7 depicts a comparison of the calibration curves for an hTSH assay. These curves indicate the results of an assay using a double-antibody immunocomplex format and two assays using a dendrimer-coupled antibody format.
Figure 8:
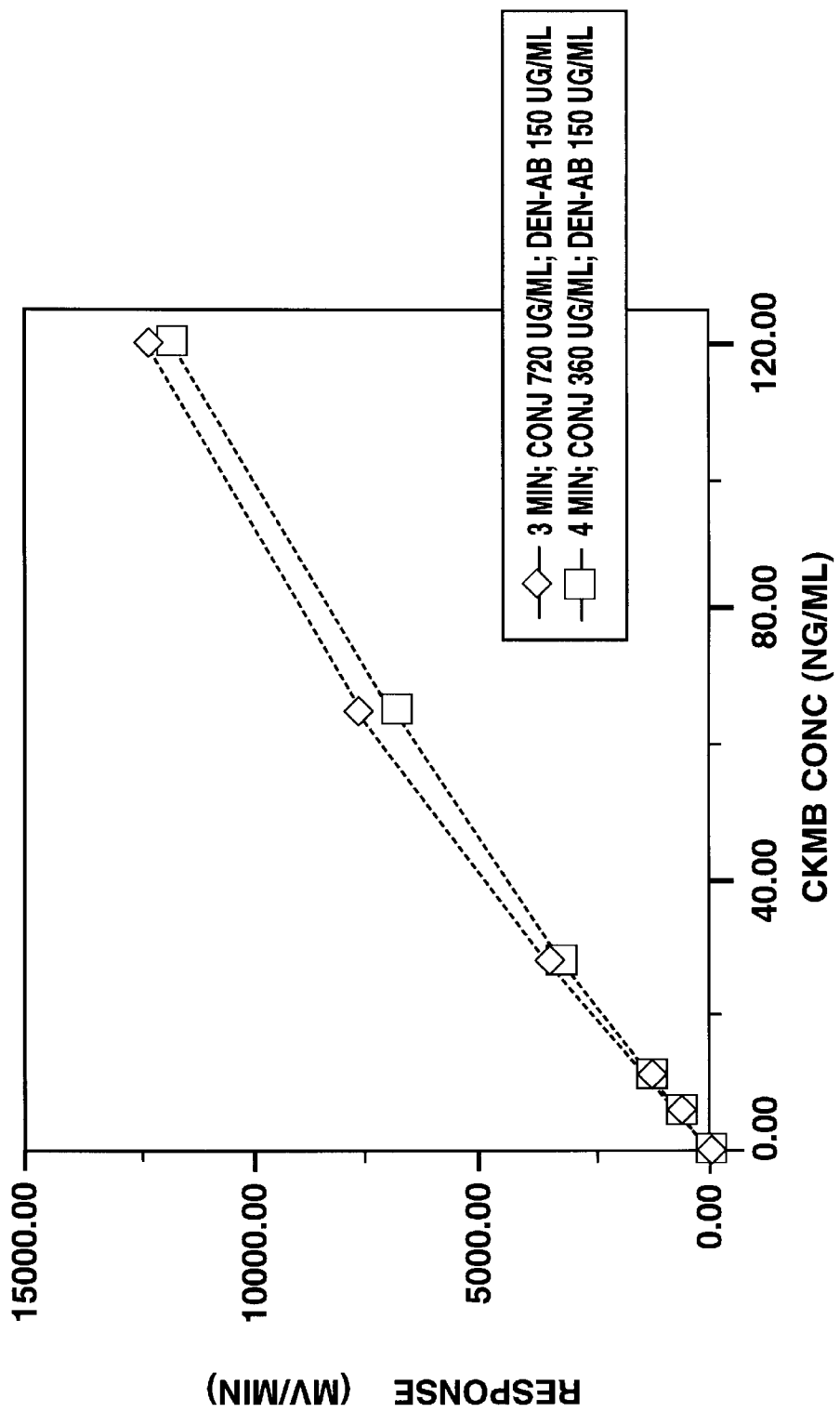
FIG. 8 depicts calibration curves obtained for CKMB assays. These curves were obtained by manipulations of the concentrations of the conjugate and the dendrimer-coupled antibody.

Full calibration curves were carried out for hTSH and CKMB assays using the manipulations described above. The calibration curves are depicted in FIGS. 7 and 8 for the hTSH and CKMB assays, respectively. As used below and in the figures, the terms "8-minute assay" and "current assay" are used interchangeably with the term "double-antibody immunocomplex format." All of these terms refer to an assay format that requires the use of two different antibodies: a first antibody specific for the analyte and a second antibody specific for the anti-analyte antibody. The antibodies are combined in a buffer, and the resulting double-antibody immunocomplex is immobilized on a solid phase prior to the addition of the sample and indicator to the solid phase. The term "in-solution assay" is used interchangeably with "solution phase format," "4-minute assay," "fast assay" and "pre-mix" assay. These terms all refer to an assay format where the dendrimer-coupled antibody, sample and/or indicator are first mixed together in a reaction solution prior to their application to the solid phase for the remainder of the assay.

FIG. 7 shows that for the hTSH assay the shape of the calibration curves for two variations of the in-solution assay was quite comparable to the shape of the calibration curve for the double-antibody immunocomplex assay. The concentrations of the conjugate and the dendrimer-coupled antibody were varied between the two assays using the dendrimer-coupled antibody format. The assay using the higher concentrations of the conjugate and the dendrimer-coupled antibody produced the fastest kinetic equilibrium, allowing completion of the assay in 3.93 minutes as compared to 4.5 minutes for the other dendrimer-coupled antibody assay and 8 minutes for the double-antibody assay format.

The inset in FIG. 7 shows that the low-end sensitivity for the hTSH assay in the in-solution format is considerably improved. In fact, the low-end sensitivity also was improved in the in-solution assay as compared to both immobilized dendrimer-coupled antibody format and an immunological immobilization (double-antibody complex) format. This improvement is due to very low nonspecific binding. The ratio of the calibrators, Cal B/Cal A and CalF/Cal A, was 4.50 and 719.5 for the in-solution assay as compared to the corresponding values of 1.67 and 91.7 respectively, for the double-antibody complex format.

Table 3 shows a comparison of assay sensitivity and amount of antibody required for the current double-antibody format as opposed to the in-solution dendrimer-antibody format for three different analytes. These assays were carried out on a Stratus® II instrument by aspirating and delivering 76 μl of a mixture containing the sample and the dendrimer-coupled antibody or double-antibody immunocomplex onto a blank tab, as described above. The assay was then completed by application of the conjugate and the substrate wash, as described above.

TABLE 3

COMPARISON OF THE CURRENT DOUBLE-ANTIBODY FORMAT AND THE IN-SOLUTION FORMAT USING E5-ANTIBODY TABS

| | Sensitivity<br>(Min. Detectable Dose) | | Primary Antibody<br>per Tab (μg) | |
| --- | --- | --- | --- | --- |
| ASSAY | CURRENT | E5-Antibody | CURRENT | E5-Antibody |
| hTSH | 0.05 μIU/ml | 0.01 μIU/ml | 3.8 | 0.09 |
| CKMB | 0.40 ng/ml | 0.14 ng/ml | 2.3 | 0.38 |
| Myoglobin | 0.37 ng/ml | 0.05 ng/ml | 3.8 | 0.17 |

Figure 9:
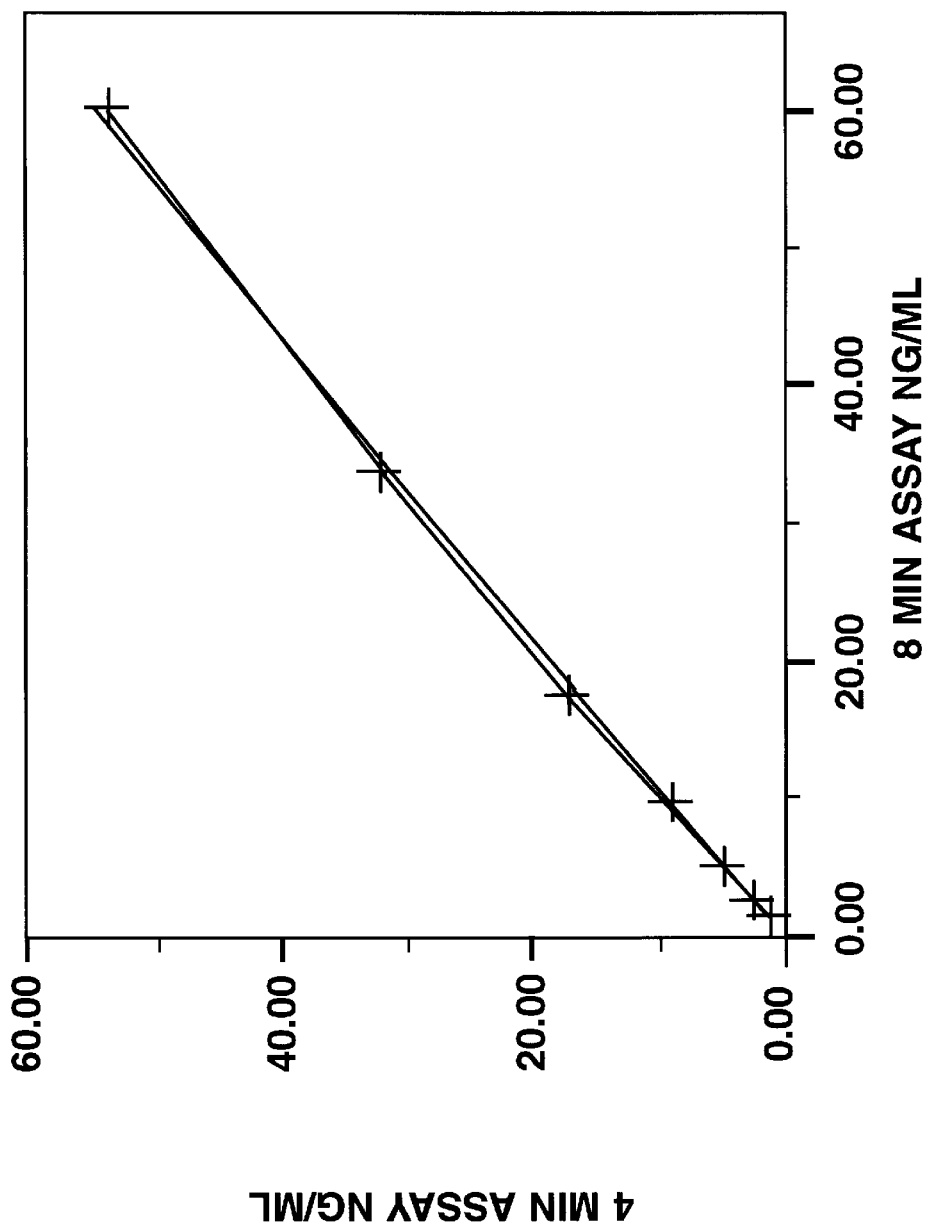
FIG. 9 depicts a comparison of the eight minute CKMB assay with the four minute assay.
Figure 10:
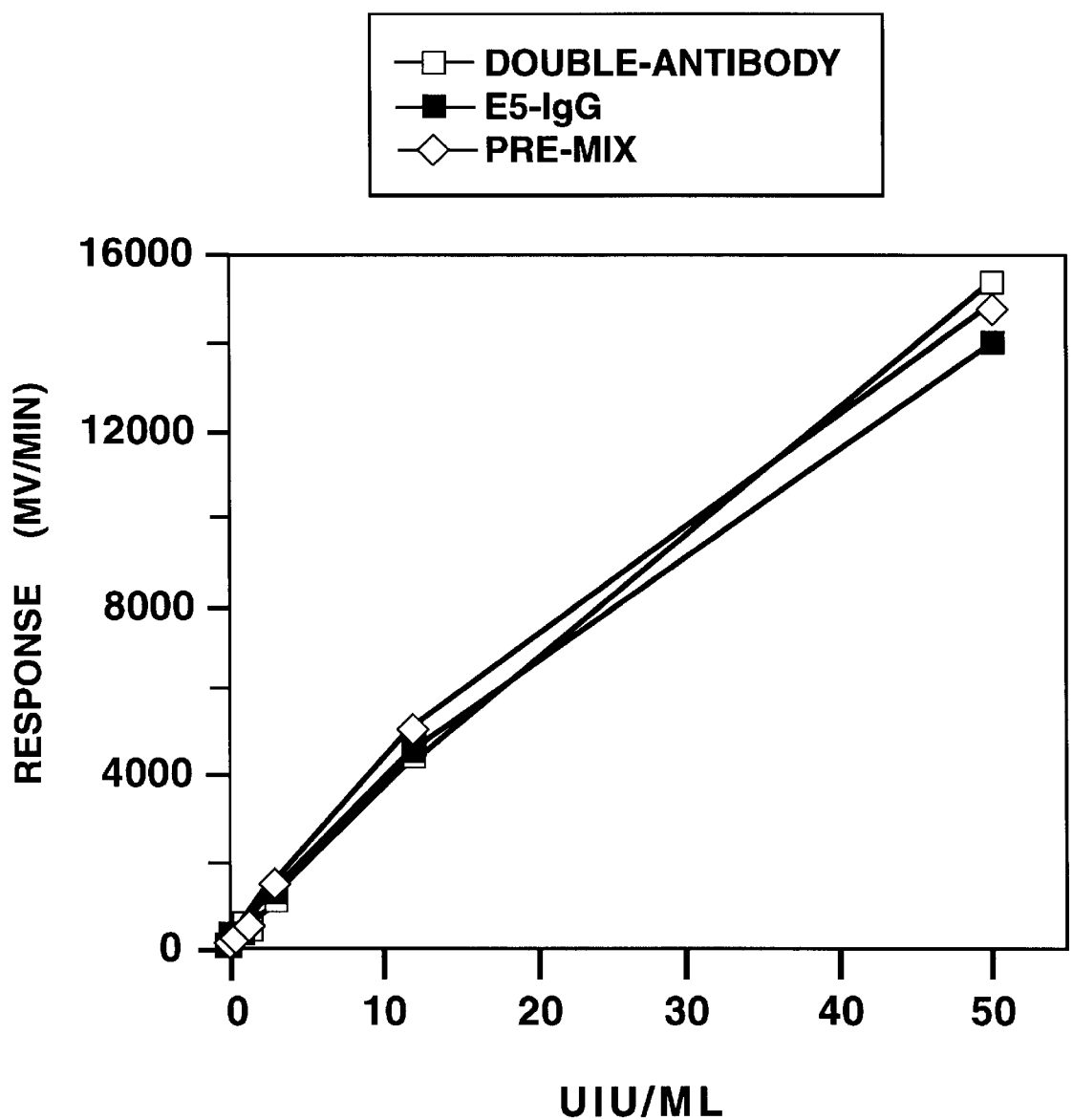
FIG. 10 depicts a comparison of calibration curves for an hTSH assay using the double-antibody format and two different formats of the dendrimer-coupled antibody assay.

FIG. 8 shows calibration curves generated for a CKMB assay in the in-solution format. These curves were obtained by manipulations of the concentrations of the conjugate and the dendrimer-coupled antibody. These manipulations achieved faster kinetic equilibrium, allowing completion of the assay in 4 or 5 minutes. A comparison of a CKMB assay using the double-antibody immunocomplex format with that of the in-solution format is shown in FIG. 9. An $R^2$ value of 0.999047 using a linear regression analysis clearly indicates that the two assays produce comparable results, giving the same analyte concentration. The faster kinetics of the in-solution assay of the present invention, however, offers the distinct advantage of giving the results in half the time as the double-antibody immunocomplex format. A similar comparison of calibration curves for an hTSH assay using the double-antibody format and two different formats of the dendrimer-coupled antibody assay is depicted in FIG. 10. The "pre-mix" format refers to the in-solution assay and the "dry tab" format refers to an assay format where the dendrimer-coupled antibody is immobilized on the solid phase prior to the addition of the sample and indicator to the solid phase. For these curves the amounts of primary antibody used per tab was 1.14 μg for the double-antibody format, 1.14 μg for the immobilized dendrimer-coupled antibody format and 0.38 μg for the in-solution dendrimer-coupled antibody format. These results clearly show that the use of a dendrimer-coupled antibody in a reaction solution prior to immobilization on a glass fiber filter improves the assay sensitivity for an analyte and also provides faster results.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method for immobilizing a plurality of specific binding assay reagents on a solid phase, comprising the steps of:
   (a) providing a dendrimer-reagent solution comprising at least one type of dendrimer-reagent complex, each said complex comprising a dendrimer coupled to at least one specific binding assay reagent, said reagent having a defined analyte specificity, said specificity differing for each said reagent;
   (b) adding a sample suspected of containing one or more analytes or receptor of said one or more analytes under conditions effecting binding of said one or more analytes or receptor of said one or more analytes to said reagent in said dendrimer-reagent solution to form an assay solution; and
   (c) applying an effective amount of said assay solution to a solid phase having interstices therein under conditions effecting immobilization of each said complex on a delimited area of said solid phase.

2. The method of claim 1, wherein said assay solution further comprises a selected amount of one or more labeled conjugates.

3. The method of claim 1, wherein said assay solution further comprises one or more labeled specific competitive reagents.

4. The method of claim 3, wherein each said specific competitive reagent is a labeled analogue of a corresponding one of said one or more analytes or receptor of said one or more analytes.

5. The method of claim 1, wherein said reagent is selected from the group consisting of antibodies, antibody fragments, specific binding proteins and analytes.

6. The method of claim 1, wherein said coupling of said reagent to said dendrimer is by C—S linkage carried out by combining SIAB-labeled moieties with sulfhydryl-containing moieties.

7. The method of claim 1, wherein said coupling of said reagent to said dendrimer is by C—S linkage carried out by combining SMCC labeled moieties with the sulfhydryl-containing moieties.

8. The method of claim 1, wherein said coupling of said reagent to said dendrimer is by C—N linkage carried out by combining aldehyde-labeled moieties with unmodified dendrimers.

9. The method of claim 1, wherein said dendrimer is an E5 dendrimer.

10. The method of claim 1, wherein said dendrimer is an N5 dendrimer.

11. A method for conducting a specific binding assay to determine the concentration or presence of one or more analytes or receptors for said analytes in a sample, comprising the steps of:
   (a) providing a dendrimer-reagent solution comprising at least one type of dendrimer-reagent complex, each said complex comprising a dendrimer coupled to at least one specific binding assay reagent, said reagent having a defined analyte specificity, said specificity differing for each said reagent;
   (b) adding said sample under conditions effecting binding of one or more analytes or receptor of said one or more analytes to said reagent in said dendrimer-reagent solution to form an assay solution;
   (c) adding an effective amount of said assay solution to a solid phase having interstices therein under conditions effecting immobilization of said complex on a delimited area of said solid phase;
   (d) applying a selected amount of one or more labeled conjugates to said delimited area under conditions effecting binding of each said conjugate to a corresponding one of said analytes or receptor of said one analyte;
   (e) determining the amount of each said conjugate bound to said corresponding analyte or receptor of said corresponding analyte on said delimited area; and
   (f) correlating said amount of each said conjugate with the concentration or presence of said corresponding analyte or receptor of said corresponding analyte in said sample.

12. The method of claim 11, wherein said reagent is selected from the group consisting of antibodies, antibody fragments, specific binding proteins and analytes.

13. The method of claim 11, wherein said coupling of said reagent to said dendrimer is by C—S linkage carried out by combining SIAB-labeled moieties with sulfhydryl-containing moieties.

14. The method of claim 11, wherein said coupling of said reagent to said dendrimer is by C—S linkage carried out by combining SMCC labeled moieties with the sulfhydryl-containing moieties.

15. The method of claim 11, wherein said coupling of said reagent to said dendrimer is by C—N linkage carried out by combining aldehyde-labeled moieties with unmodified dendrimers.

16. The method of claim 11, wherein said dendrimer is an E5 dendrimer.

17. The method of claim 11, wherein said dendrimer is an N5 dendrimer.

18. A method for conducting a specific binding assay to determine the concentration or presence of one or more analytes or receptors for said analytes in a sample, comprising the steps of:
   (a) providing a dendrimer-reagent solution comprising at least one type of dendrimer-reagent complex, each said complex comprising a dendrimer coupled to at least one specific binding assay reagent, said reagent having a defined analyte specificity, said specificity differing for each said reagent;
   (b) adding said sample and a selected amount of one or more labeled specific competitive reagents, each said competitive reagent corresponding to one of said analytes or receptor of said one analyte, under conditions effecting binding of each said competitive reagent and said one or more analytes or receptor of said one or more analytes to said complexes in said dendrimer-reagent solution to form a competitive assay solution;
   (c) adding an effective amount of said competitive assay solution to a solid phase having interstices therein under conditions effecting immobilization of said complex on a delimited area of said solid phase;
   (d) determining the amount of each said competitive reagent bound to said complexes; and
   (e) correlating said amount of each said competitive reagent with the concentration or presence of said corresponding analyte or receptor of said corresponding analyte in said sample.

19. The method of claim 18, wherein each said specific competitive reagent is a labeled analogue of said corresponding analyte or receptor of said corresponding analytes.

20. The method of claim 18, wherein said reagent is selected from the group consisting of antibodies, antibody fragments, specific binding proteins and analytes.

21. The method of claim 18, wherein said coupling of said reagent to said dendrimer is by C—S linkage carried out by combining SIAB-labeled moieties with sulfhydryl-containing moieties.

22. The method of claim 18, wherein said coupling of said reagent to said dendrimer is by C—S linkage carried out by combining SMCC labeled moieties with the sulfhydryl-containing moieties.

23. The method of claim 18, wherein said coupling of said reagent to said dendrimer is by C—N linkage carried out by combining aldehyde-labeled moieties with unmodified dendrimers.

24. The method of claim 18, wherein said dendrimer is an E5 dendrimer.

25. The method of claim 18, wherein said dendrimer is an N5 dendrimer.

26. A method for conducting a specific binding assay to determine the concentration or presence of one or more analytes or receptors for said analytes in a sample, comprising the steps of:

(a) providing a dendrimer-reagent solution comprising at least one type of dendrimer-reagent complex, each said complex comprising a dendrimer coupled to at least one specific binding assay reagent, said reagent having a defined analyte specificity, said specificity differing for each said reagent;

(b) adding said sample and a selected amount of one or more labeled conjugates under conditions effecting binding of each said conjugate to a corresponding one of said analytes or receptor of said one analyte and binding of said one or more analytes or receptor of said one or more analytes to said reagent in said dendrimer-reagent solution to form an assay solution;

(c) adding an effective amount of said assay solution to a solid phase having interstices therein under conditions effecting immobilization of said complex on a delimited area of said solid phase;

(d) determining the amount of each said conjugate bound to said corresponding analyte or receptor of said corresponding analyte on said delimited area; and (e) correlating said amount of each said conjugate with the concentration or presence of said corresponding analyte or receptor of said corresponding analyte in said sample.

27. The method of claim 26, wherein said reagent is selected from the group consisting of antibodies, antibody fragments, specific binding proteins and analytes.

28. The method of claim 26, wherein said coupling of said reagent to said dendrimer is by C—S linkage carried out by combining SIAB-labeled moieties with sulfhydryl-containing moieties.

29. The method of claim 26, wherein said coupling of said reagent to said dendrimer is by C—S linkage carried out by combining SMCC labeled moieties with the sulfhydryl-containing moieties.

30. The method of claim 26, wherein said coupling of said reagent to said dendrimer is by C—N linkage carried out by combining aldehyde-labeled moieties with unmodified dendrimers.

31. The method of claim 26, wherein said dendrimer is an E5 dendrimer.

32. The method of claim 26, wherein said dendrimer is an N5 dendrimer.

* * * * *

UNITED STATES PATENT AND TRADEMARK OFFICE
CERTIFICATE OF CORRECTION

PATENT NO. : 5,898,005
DATED : April 27, 1999
INVENTOR(S) : Pratap Singh, et. al.

It is certified that error appears in the above-indentified patent and that said Letters Patent is hereby corrected as shown below:

Column 8, Line 61: Delete "calorimetric" and insert --colorimetric--.

Signed and Sealed this

Fifth Day of October, 1999

Attest:

Q. TODD DICKINSON

Attesting Officer

Acting Commissioner of Patents and Trademarks